(12) United States Patent
Daulton

(10) Patent No.: US 7,766,216 B2
(45) Date of Patent: Aug. 3, 2010

(54) SELF-CENTERING BRAZE ASSEMBLY METHODS

(75) Inventor: Jay Daulton, Gilroy, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 241 days.

(21) Appl. No.: 11/557,043

(22) Filed: Nov. 6, 2006

(65) Prior Publication Data
US 2007/0057025 A1   Mar. 15, 2007

Related U.S. Application Data

(62) Division of application No. 10/609,457, filed on Jun. 27, 2003, now Pat. No. 7,132,173.

(60) Provisional application No. 60/392,475, filed on Jun. 28, 2002.

(51) Int. Cl.
    *B23K 31/02* (2006.01)
(52) U.S. Cl. .................................. 228/122.1
(58) Field of Classification Search ............... 228/122.1
    See application file for complete search history.

(56) References Cited

U.S. PATENT DOCUMENTS 4,919,135 A * 4/1990 Phillips et al. .............. 607/121
4,991,582 A * 2/1991 Byers et al. .................. 607/2
5,013,612 A * 5/1991 Hunt et al. .................. 428/552

FOREIGN PATENT DOCUMENTS

WO   WO 00/56677   * 9/2000

* cited by examiner

*Primary Examiner*—Jessica L Ward
*Assistant Examiner*—Nicholas P D'Aniello
(74) *Attorney, Agent, or Firm*—Frommer Lawrence & Haug LLP; Bruce E. Black

(57) ABSTRACT

Braze and electrode wire assemblies, e.g., used with an implantable microstimulator, include a wire welded in the through-hole of an electrode, which electrode is brazed to a ceramic case that is brazed to a metal ring that is welded to a metal can. The braze joints are step or similar joints that self-center the case, provide lateral support during braze assembly, and provide increased surface area that prevents braze material from exuding from the joints. The end of the ceramic case that is brazed to the metal ring need not be specially machined. The shell has a reference electrode on one end and an active electrode on the other, and is externally coated on selected areas with conductive and non-conductive materials.

20 Claims, 15 Drawing Sheets

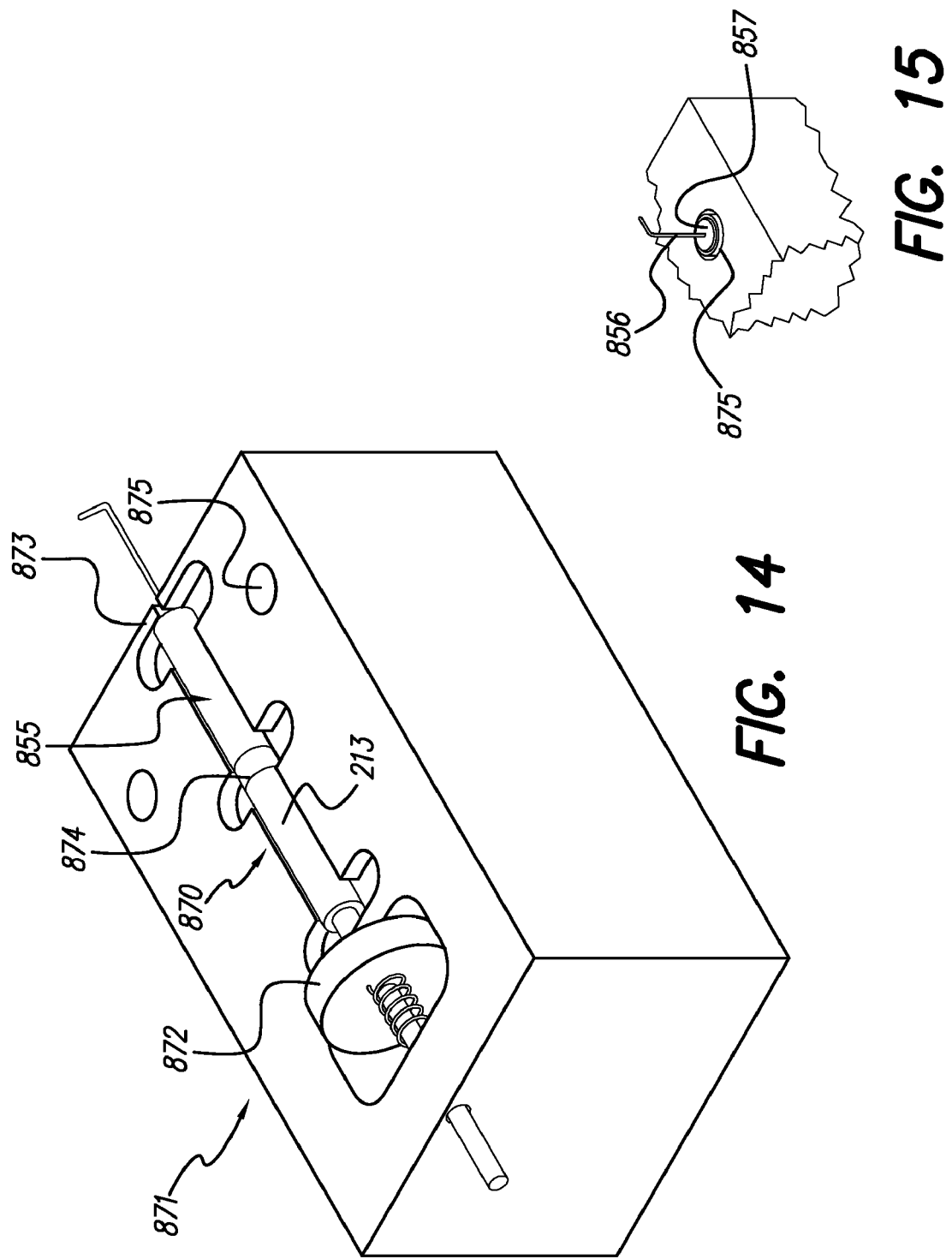

SELF-CENTERING BRAZE ASSEMBLY METHODS

The present application is a divisional of U.S. application Ser. No. 10/609,457, filed Jun. 27, 2003, issuing on Nov. 7, 2006 as U.S. Pat. No. 7,132,173; which claims the benefit of U.S. Provisional Patent Application Ser. No. 60/392,475, filed Jun. 28, 2002, which applications are incorporated herein by reference in their entireties.

FIELD OF THE INVENTION

The present invention relates to braze assemblies and more particularly to self-centering braze assemblies of ceramic and metallic materials for applications such as medical devices, electrical connectors, electronics packages, and structural components.

BACKGROUND OF THE INVENTION

Many products made of different materials with different properties are manufactured by sealing the different materials together. A seal between two different materials can be produced by welding, gluing, brazing, or similar processes. Brazing is the process of soldering two materials with different properties, such as ceramic and metal, together using a hard solder with a relatively high melting point. One can create a very strong and lasting seal between two different materials by employing the braze materials and methods described in the prior art. Many products benefit from brazing, including medical devices such as implantable microstimulators. A strong hermetic seal is required between ceramic and metallic materials of the outer case of some microstimulators.

Implantable microstimulators known as Bion® devices are characterized by a small, cylindrical housing which contains electronic circuitry for producing electric currents between spaced electrodes. The microstimulators are implanted proximate to the target tissue, and the currents produced by the electrodes stimulate the tissue to reduce symptoms or otherwise provide therapy for various disorders. Microstimulators often include valuable electronic circuitry, batteries, and other components that must be hermetically sealed within a secure case in order to protect the inner components of the microstimulator from damage by surrounding tissue and in order to protect a patient from harm caused by a malfunctioning microstimulator.

Radio-frequency powered and battery powered microstimulators are described in the art. See, for instance, U.S. Pat. No. 5,193,539 ("Implantable Microstimulator); U.S. Pat. No. 5,193,540 ("Structure and Method of Manufacture of an Implantable Microstimulator"); U.S. Pat. No. 5,312,439 ("Implantable Device Having an Electrolytic Storage Electrode"); U.S. Pat. No. 6,185,452 ("Battery-Powered Patient Implantable Device"); U.S. Pat. Nos. 6,164,284 and 6,208,894 (both titled "System of Implantable Device for Monitoring and/or Affecting Body Parameters"). The '539, '540, '439, '452, '284, and '894 patents are incorporated herein by reference in their entirety.

Microstimulators that prevent and/or treat various disorders associated with prolonged inactivity, confinement or immobilization of one or more muscles are taught, e.g., in U.S. Pat. No. 6,061,596 ("Method for Conditioning Pelvis Musculature Using an Implanted Microstimulator"); U.S. Pat. No. 6,051,017 ("Implantable Microstimulator and Systems Employing the Same"); U.S. Pat. No. 6,175,764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). The techniques described in these additional patents, including power charging techniques, may also be used with the present invention. The '596, '017, '764, '965, '455, and '032 patents are incorporated herein by reference in their entirety.

The various types of microstimulators known in the art, and other products in other arts, often employ brazing materials and methods to create hermetic seals for the cases that house the inner components of such devices. For example, U.S. Pat. No. 6,221,513, which patent is incorporated herein by reference in its entirety, describes methods for hermetically sealing ceramic to metallic surfaces and assemblies that incorporate ceramic to metallic seals. The '513 patent discloses a brazed butt joint, a brazed bevel joint, and a braze joint between a metal end cap and a ceramic open-ended cylinder. Another example, International Publication No. WO 00/56394, which publication is incorporated herein by reference in its entirety, describes a ceramic case assembly for a microstimulator. The '394 publication discloses a brazed butt joint, a brazed internal step joint for self-jigging, and a braze joint between a metal end cap and a ceramic open-ended cylinder. Yet another example, International Publication No. WO 00/56677, which publication is also incorporated herein by reference in its entirety, describes both a self-jigging bevel joint and a self-jigging internal step joint for a metal-ceramic braze bond. In a final example, U.S. Pat. No. 4,991,582, which patent is also incorporated herein by reference in its entirety, discloses a metal to machined ceramic braze bond using a self-jigging step joint.

Although the various types of hermetic seals and braze joints known in the art may be useful for microstimulators and other products, significant improvements upon these seals and joints are still possible and desirable, particularly relative to a braze joint creating a strong and safe hermetic seal that can be successfully produced on a consistent basis and in a cost effective manner.

For example, the '513 patent and the '394 and '677 publications are likely to suffer from the undesirable effects of braze material that exudes from the joint to the outer surface of a device case during assembly. When braze material exudes, during assembly, to the outer surface of the case, the material cools after the brazing process is complete to create a sharp metallic burr, e.g., on the outside surface of the device case. This burr, if not removed, could cause significant discomfort, damage, and injury to a patient when the microstimulator is implanted. Yet, removing the dangerous burr after braze assembly using any technique—including chipping, sanding, shaving, laser cutting or other method—is certain to increase the manufacturing time and cost and is very likely to compromise the strength of the braze bond.

Further, the '582 patent discloses a step joint between a metal member and a ceramic case, which ceramic case is machined to include a step that specifically fits in communication with the metal member at the joint. Machining a ceramic case often leaves residual cracks and weakens the case, especially where the wall of the ceramic case is thin.

Therefore, a need exists for a braze joint assembly that improves upon the prior art by providing a strong ceramic case at the braze joint and a means for inhibiting braze material exudation.

SUMMARY OF THE INVENTION

The present invention addresses the above and other needs by providing a self-centering braze assembly for hermetically sealing the metal and ceramic materials of various products, e.g., a Bion® or other microstimulator. The present invention also describes the method of assembling and brazing the materials used to create the hermetic seal of a self-centering braze assembly. The self-centering braze assembly includes increased surface area at the braze joint. This increased surface area permits the use of an adequate amount of braze material that is necessary to create a strong braze joint. At the same time, the increased surface area inhibits braze material from exuding from the braze joint. Further, the self-centering braze assembly includes a flange on a metal ring that encompasses the external, or outer-circumferential, surface of the ceramic case at the braze joint. This flange acts as a dam that inhibits braze material from exuding from the braze joint. Further, the present invention includes a ceramic case that need not be machined at the braze joint and is therefore stronger at the braze joint.

The self-centering braze assembly of the present invention is made from biocompatible, hermetically-sealable material. A first braze assembly of the present invention includes a ceramic case brazed to a metal ring using braze material. The braze material is a titanium/nickel alloy or similar alloy capable of adhering to and creating a strong metal bond between ceramic and metal during a brazing process. The metal ring is manufactured using titanium, or other biocompatible metal, and includes an external step joint, external step/bevel joint, or other joint with at least one external flange. Braze, ceramic, and metal materials and brazing methods useful with the present invention include those materials and methods known in the art, such as those disclosed in U.S. Pat. No. 6,221,513, and International Publication Nos. WO 00/56677 and WO 00/56394.

The at least one external flange communicates with the outer circumference of the ceramic case. The at least one external flange and step, or other surface, of the metal ring are long enough to provide adequate surface area in contact with the ceramic case, so as to prevent braze material from exuding from the joint along the outer circumferential surface of the joint while allowing an appropriate amount of braze material to be applied to the joint in order to create a strong bond. Both the external flange communicating with the outer surface of the ceramic case and the increased surface area of the present invention are significant improvements over the prior art, including the '513 patent and the '394 and '677 publications. The '513 patent and the '394 and '677 publications fail to teach, inter alia, a braze assembly employing both an external flange that communicates with the outer diameter of a ceramic case and also a flange and step or other joint with adequate or increased surface area.

The end of the ceramic case that communicates with the metal ring need not be specially machined to be able to form a mutually-butted step joint, or other mutual joint, with the metal ring. In other words, the end of the ceramic case that communicates with the metal ring need not be cut, shaped, or machined as a step, bevel, or other similar surface. Rather, the end of the ceramic case that communicates with the metal ring is a butted end. The butted end of the ceramic case is a significant improvement over U.S. Pat. No. 4,991,582 which uses a machined ceramic case that is susceptible to residual cracks that ultimately lead to a weakened braze joint. The present invention, by providing a ceramic case with a butted end, is capable of employing ceramic cases with very thin walls, e.g., approximately 0.010 inches thick.

The present invention also includes a second braze assembly, which second braze assembly includes a ceramic close-ended can, braze material, and an electrode. A small hole is defined in the end of a substantially closed end of the ceramic can, the inner circumferential surface of which communicates with an outer circumferential surface of a pin of the electrode. A bottom surface of the electrode communicates with a bottom surface of the substantially closed end of the ceramic can, between which surfaces the braze material has adequate surface area to melt and bond without exuding from the exterior circumference of the joint. The increased surface area of the present invention is a significant improvement over the prior art, including International Publication No. WO 090/56394, which describes a braze assembly between a metal end cap and a ceramic open-ended cylinder, not a ceramic close-ended can. The width of the wall of the ceramic open-ended cylinder provides insufficient surface area which, when placed in communication with the metal end cap, allows braze material to exude and establishes a relatively weak braze bond.

The present invention also includes a through-hole assembly and method of assembly for attaching a wire to a capacitor and an electrode.

Methods of manufacturing/assembling a hermetically sealed housing for the internal components of a microstimulator are described herein. Also described herein are methods and materials for externally coating the hermetically sealed cylindrical housing to protect the internal components.

Embodiments described herein may include some or all of the items mentioned above. Additional embodiments will be evident upon further review of the present disclosure.

BRIEF DESCRIPTION OF THE DRAWINGS

The above and other aspects of the present invention will be more apparent from the following more particular description thereof, presented in conjunction with the following drawings wherein:

FIG. 14 is a perspective view of a microstimulator horizontally housed in a carrier;

FIG. 15 is a perspective view of a microstimulator vertically housed in a carrier.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention may be used with numerous devices. Such devices may include implantable medical devices, such as microstimulators. However, as will be understood by those of skill in the art, the present invention may be used with other types of devices. The exemplary medical device that will be used herein to describe the systems and methods of the present invention is a small, implantable stimulator, and more particularly a microstimulator known as a Bion® microstimulator.

The Bion® microstimulator has a substantially cylindrical shape (other shapes are possible) and at least portions of it are hermetically sealed using the methods and structure of the present invention. The Bion® microstimulator includes a processor and other electronic circuitry that allow it to generate stimulus pulses that are applied to a patient through electrodes in accordance with a program that may be stored, if necessary or desired, in programmable memory.

The Bion® microstimulator manufactured in part by the present invention includes internal and external components. The internal components of the Bion® microstimulator are encompassed by a hermetically sealed metal and ceramic case, which case is welded and brazed together using the self-centering braze assembly structures and methods of the present invention.

Figure 1A:
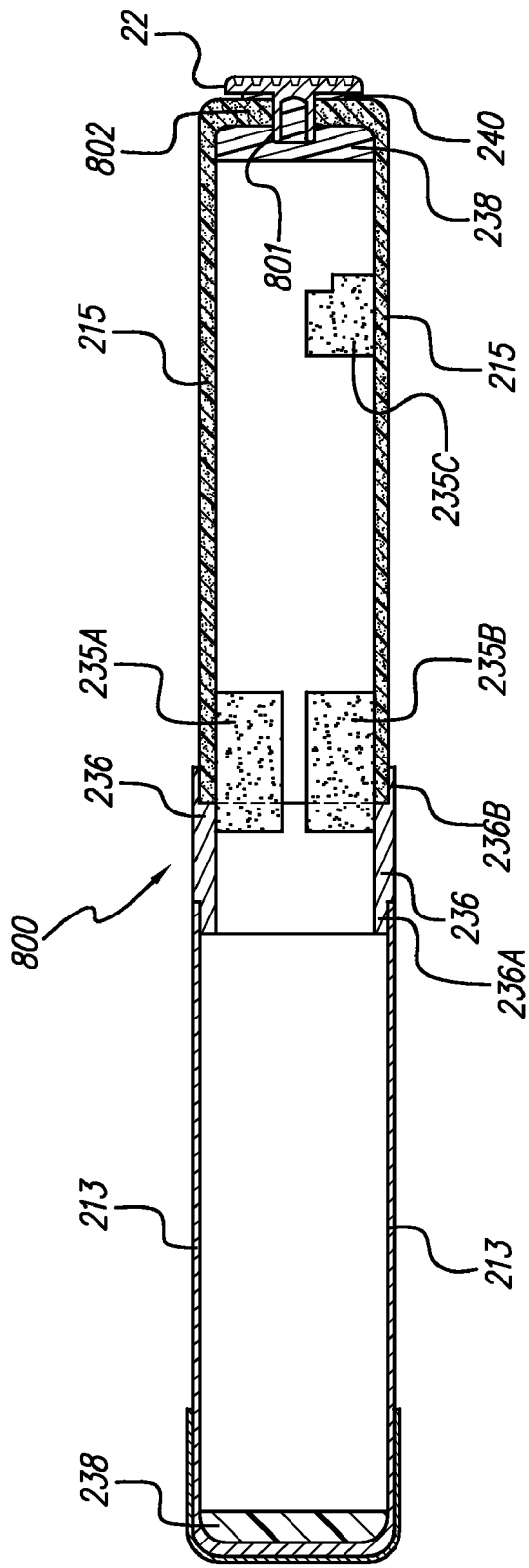
FIG. 1A is a cross-sectional view of a Bion® shell of the present invention.

FIG. 1A is a cross-sectional view of a Bion® microstimulator shell 800 assembled using the present invention. The shell 800 encapsulates the internal components of the Bion® microstimulator. The shell 800 is an exemplary hermetically-sealed housing which consists of, for instance, two cylindrical cases, or cans: a metal or metal alloy case, or can, 213 and a ceramic case, or can, 215. Alternative materials and shapes for the shell may also be used. Alternative materials include stabilized zirconia, partially stabilized zirconia, yttria-stabilized zirconia, tretragonal zirconia, magnesia-stabilized zirconia, ceria-stabilized zirconia, calcia-stabilized zirconia, alumina, silicon nitride, silicon carbide, titanium carbide, tungsten carbide, titanium nitride, silicon aluminum oxynitride (sialon), graphite, titanium di-boride, boron carbide, molybdenum disilicide, copper, titanium-niobium, titanium-tantalum, molybdenum, and zirconium.

The metal or metal alloy case 213 may be manufactured from an alloy with low interstitial defects, e.g., a titanium 6/4 alloy, and may have a wall approximately 0.003 inches thick. The case 213 may be precision screw machined from rod stock and preferably includes a closed end machined design that eliminates the need to laser weld an end cap at the end of the case 213.

A connector, or metal ring, 236 made from metal or metal alloy, e.g., titanium 6/4 alloy, is brazed with a titanium nickel alloy (or other suitable material) to the ceramic case 215. During the brazing process, the braze assembly (consisting of the ceramic case 215, the connector 236, and the titanium nickel alloy) is gradually heated in a vacuum until the titanium nickel alloy forms a liquidus. Then the braze assembly is gradually cooled until the braze material forms a solidus.

Titanium nickel alloys used with the present invention include proportions of titanium to nickel similar to those disclosed in the prior art, including U.S. Pat. No. 6,221,513 and International Publication Nos. WO 00/56394 and WO 00/56677. The connector 236 has an internal flange 236A and an outside flange 236B (also referred to herein as "external flange" or "exterior flange"), which flanges serve to "self-center" the braze assembly. The internal flange 236A and the connector 236 are laser welded, or otherwise permanently attached, to case 213. The connector 236 may be manufactured from an alloy with low interstitial defects and may have an external flange 236B approximately 0.003 inches thick. The external flange 236B is long enough to supply an adequate surface area in which the connector 236 is brazed to the ceramic case 215 using an amount of braze material adequate to create a strong hermetic seal without permitting the braze material to exude from the braze joint to the exterior surface of the shell 800. The external flange 236B also serves to wick surplus braze material away from the inner diameter of the shell 800 as a result of the surface tension of the braze material.

The ceramic case, or can, 215 has a wall thickness at the braze joint of approximately 0.010 inches and may be manufactured from solid sintered stock. The ceramic case, or can, 215 may instead be manufactured from a near net shape sintered can where the outer diameter of can 215 is held to a tolerance of +/−0.0002 inches in order to ensure that braze joint strength remains consistent. The ceramic can 215 has a substantially closed-end 802 defining a hole with a relatively narrow diameter.

Before inserting the internal components and before securing the mating ends, conductive silicone adhesive 238, as shown in FIG. 1A, may be applied to the inside end of the ceramic shell as well as to the inside end of the titanium shell. A molecular sieve moisture getter material may also be added to areas 235A, 235B, and 235C at appropriate moments during the assembly of the internal components, but preferably before the brazing process is initiated. The moisture getter material serves to absorb moisture that might otherwise accumulate on sensitive internal components during brazing or welding processes.

A self-centering button electrode 22 is made from titanium 6/4 or other suitable material and is plated with a 3 micron iridium coating or other suitable conductive coating. A titanium/nickel alloy 240 or other suitable material is used to braze the button electrode 22 to the ceramic case 215. The electrode 22 has a pin 801 with a relatively narrow diameter. The outer circumferential surface of the pin 801 communicates with the inner surface of the closed end 802 of the can 215.

Figure 1B:
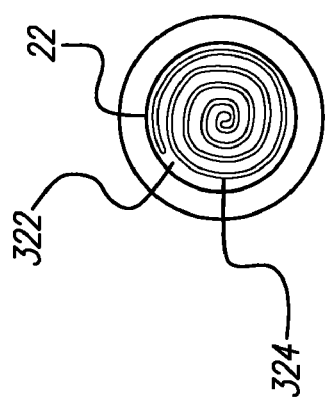
FIG. 1B is an end view of the Bion® shell of FIG. 1A.

FIG. 1B is an end view of the Bion® microstimulator shown in FIG. 1A. The self-centering button electrode 22 with a spiral groove 324 cut into its surface is made from titanium 6/4 or other suitable material and is plated with an iridium coating or other suitable conductive coating. The spiral groove 324 is cut into a stimulating surface 322 of the electrode 22. The spiral groove 324 is just one example of groove shapes that may be used; other shapes and patterns, such as a cross hatch pattern, a concentric ring pattern, a parallel line pattern, or other pattern that increases the surface area of the stimulating surface 322 may also/instead be used on button shaped electrodes, sphere shaped electrodes, or otherwise shaped electrodes. The groove 324 increases the conductive surface area 322 of the electrode 22.

The sharp edges in the groove 324 force a more homogeneous current distribution over the surface 322 and decrease the chances of electrode corrosion over time. The corrosion effect which may affect the electrode 22 is also known as biofouling, which is the gradual accumulation of bacteria on the surface of the electrode 22 once immersed in body fluid. When current is injected into body fluids, an electrochemical reaction occurs, producing large amounts of current density, which can contribute to the accumulation of bacteria. The spiral groove 324 or similar groove helps reduce the current density along the sharp groove edges. A tool made in the shape of a trapezoid or similar shape is used to cut the groove 324 into a spiral or other shape. Other methods of cutting the groove 324 may be used, e.g., ion beam etching.

The braze, ceramic, and metal materials and the brazing methods known in the art, such as those disclosed in U.S. Pat. No. 6,221,513, and International Publication Nos. WO 00/56677 and WO 00/56394, may be used with the present invention. The '513 patent provides helpful examples of methods for brazing the materials of the present invention.

FIGS. 2A to 5B portray various braze joints, before and after assembly, that are similar to those disclosed by the prior art.

Figure 2A:
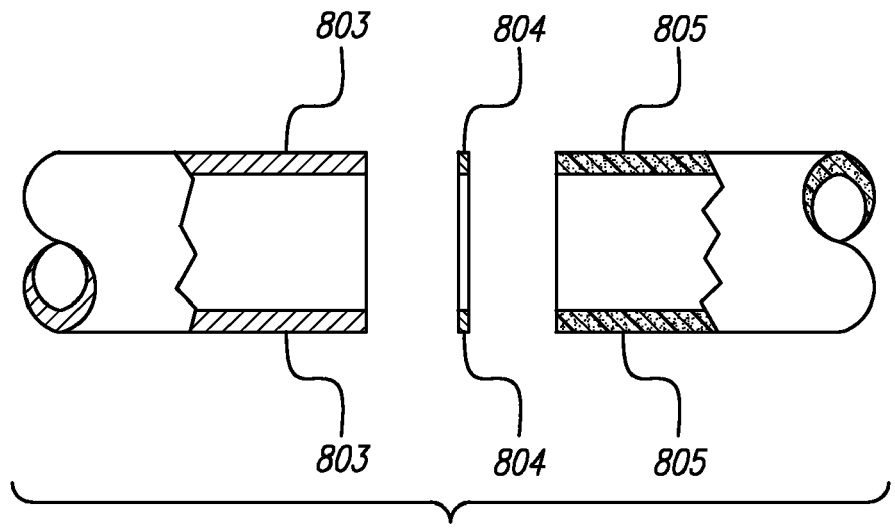
FIG. 2A is a cross-sectional view of an assembly similar to that disclosed by the prior art of a metal band, a high temperature braze preform in the shape of a ring, and a ceramic case before assembly.
Figure 2B:
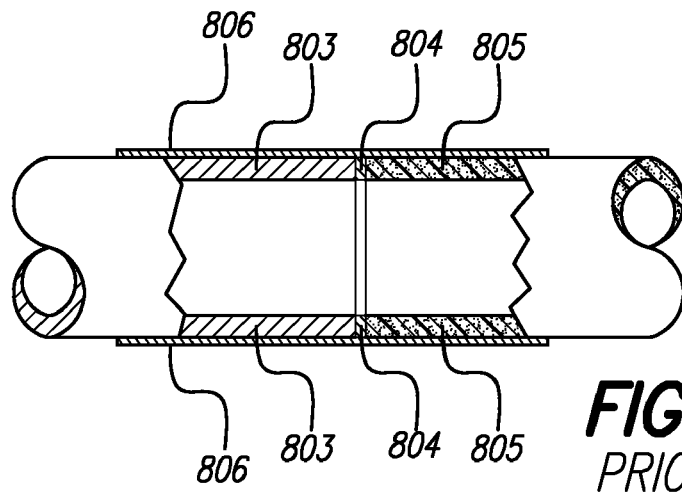
FIG. 2B is a cross-sectional view of the metal band, the high temperature braze preform, and the ceramic case of FIG. 2A aligned with a cylinder during assembly.
Figure 2C:
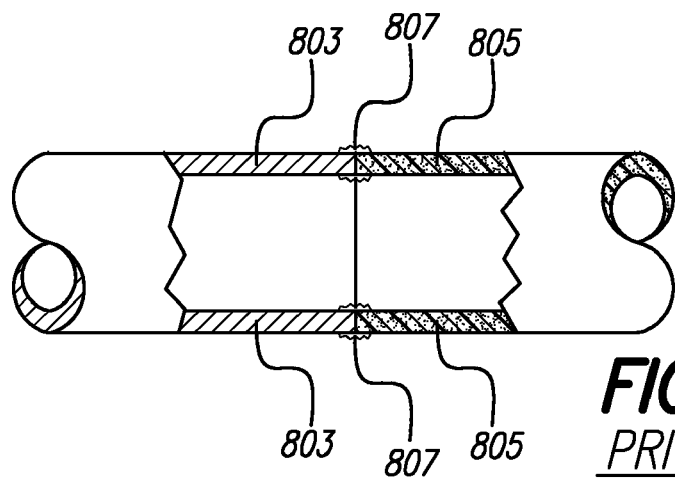
FIG. 2C is a cross-sectional view of the metal band and ceramic case of FIG. 2A after assembly.

FIG. 2A is a cross-sectional view of an assembly similar to that disclosed by the prior art of a metal band 803, a high temperature braze preform 804 in the shape of a ring, and a ceramic case 805 before assembly. FIG. 2B is a cross-sectional view of the metal band 803, the high temperature braze preform 804, and the ceramic case 805 of FIG. 2A aligned with a cylinder 806 during assembly. FIG. 2C is a cross-sectional view of the metal band 803 and the ceramic case 805 of FIG. 2A after assembly. Because the metal band 803 and the ceramic case 805 form a butt joint, and because this joint provides a minimal amount of surface area to which braze material may bond, the braze preform 804 melts during assembly and often exudes from the joint and cools after assembly to form a sharp ridge 807 of braze material along the exterior surface of the joint. The sharp ridge 807 should not be allowed to remain on the exterior surface of any consumer product, especially an implantable medical device. Permitting the sharp ridge 807 of metallic material to remain on the outer case of an implantable medical device would expose a patient to unnecessary danger. Therefore, it is important to remove the sharp ridge 807. Unfortunately, removing the sharp ridge 807 by machining or other process is certain to add time and expense to the assembly procedure and is very likely to weaken the braze joint as a result. An improvement upon the braze joint of FIGS. 2A to 2C would prevent the sharp ridge 807 from forming during the braze assembly process. Such an improvement is provided by the present invention.

Further, the butt joint of FIGS. 2A to 2C lacks substantial lateral support needed both during and after assembly. During assembly, the metal band 803 and the ceramic case 805 may be compressed towards each other with tremendous pressure. A substantial amount of pressure is desired to create a very strong braze joint. However, the butt joint assembly of FIGS. 2A to 2C likely lacks the lateral support necessary to prevent the assembly from buckling under a preferred amount of pressure without the aid of a support member such as a cylinder 806. Further, the butt joint assembly of FIGS. 2A to 2C may lack adequate lateral support to maintain a strong braze for the life and use of the product. Another improvement upon the butt joint of FIGS. 2A to 2C would provide a structural joint with more lateral support than a butt joint. Such an improvement is provided by the present invention.

Figure 3A:
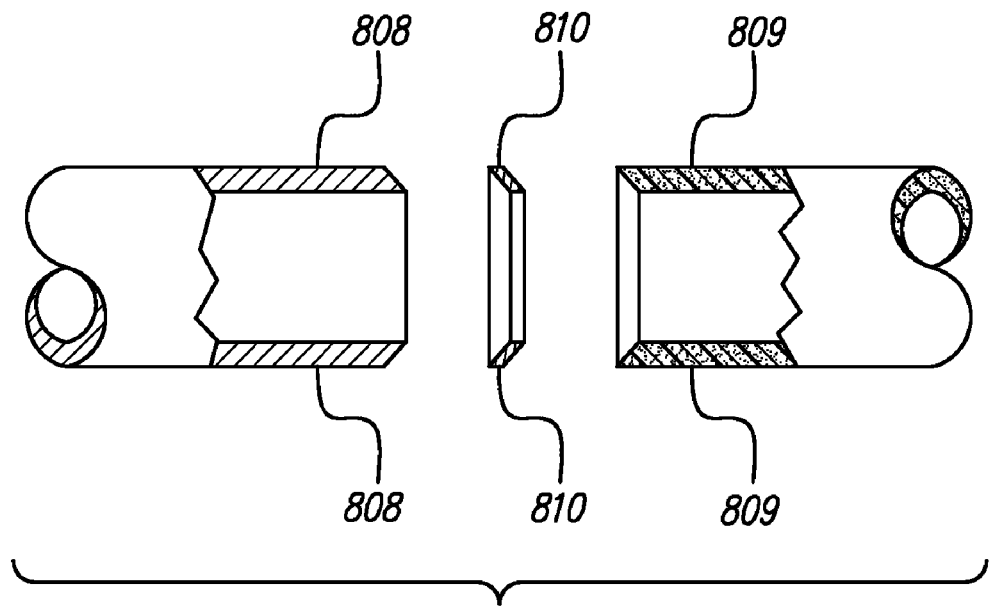
FIG. 3A is a cross-sectional view of an assembly similar to that disclosed by the prior art of a metal or metal alloy cylinder, a ceramic cylinder, and a braze preform before assembly.
Figure 3B:
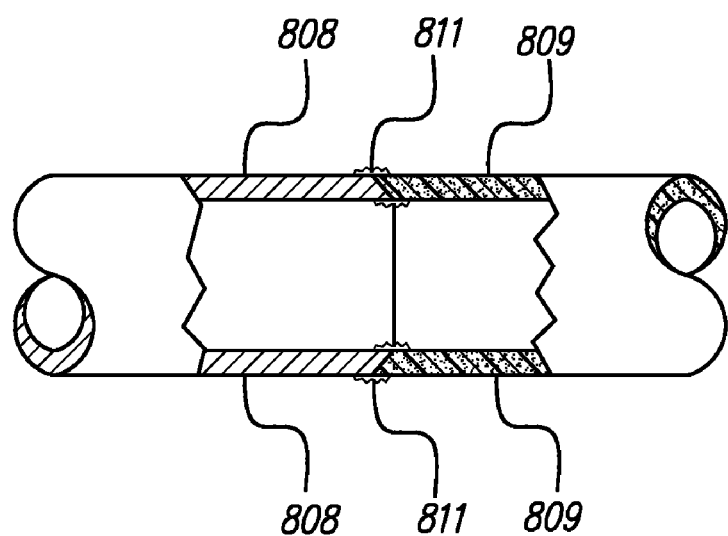
FIG. 3B is a cross-sectional view of the metal or metal alloy cylinder and the ceramic cylinder of FIG. 3A forming a self-jigging bevel joint after assembly.

FIG. 3A is a cross-sectional view of an assembly similar to that disclosed by the prior art of a metal or metal alloy cylinder 808, a ceramic cylinder 809, and a braze preform 810 before assembly. FIG. 3B is a cross-sectional view of the metal or metal alloy cylinder 808 and the ceramic cylinder 809 of FIG. 3A forming a self-jigging bevel joint after assembly. Because the metal or metal alloy cylinder 808 and the ceramic cylinder 809 form a bevel joint, and because this joint only provides slightly more surface area for braze material than a butt joint, the braze preform 810 melts during assembly and often exudes from the joint and cools after assembly to form a sharp ridge 811 of braze material along the exterior surface of the joint. The sharp ridge 811 should not be allowed to remain on the exterior surface of any consumer product, especially an implantable medical device. Permitting the sharp ridge 811 of metallic material to remain on the outer case of an implantable medical device would expose a patient to unnecessary danger. Therefore, it is important to remove the sharp ridge 811. Unfortunately, removing the sharp ridge 811 by machining or other process is certain to add time and expense to the assembly procedure and is very likely to weaken the braze joint as a result. An improvement upon the braze joint of FIGS. 3A and 3B would prevent the sharp ridge 811 from forming during the braze assembly process. Such an improvement is provided by the present invention.

Further, the bevel joint of FIGS. 3A and 3B lacks substantial lateral support needed both during and after assembly. During assembly, the metal or metal alloy cylinder 808 and the ceramic cylinder 809 may be compressed towards each other with tremendous pressure. A substantial amount of pressure is desired to create a very strong braze joint. However, the bevel joint assembly of FIGS. 3A and 3B likely lacks the lateral support necessary to prevent the assembly from buckling under a preferred amount of pressure. Further, the bevel joint assembly of FIGS. 3A and 3B may lack adequate lateral support to maintain a strong braze for the life and use of the product. Another improvement upon the braze joint of FIGS. 3A and 3B would provide a structural joint with more lateral support than a bevel joint. Such an improvement is provided by the present invention.

Figure 4A:
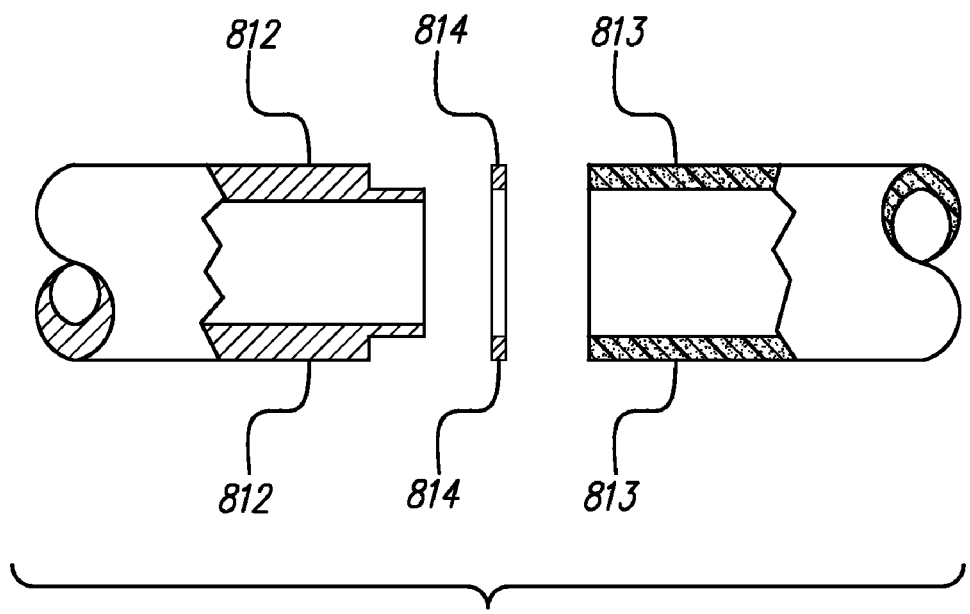
FIG. 4A is a cross-sectional view of an assembly similar to that disclosed by the prior art of a metal or metal alloy cylinder, a ceramic cylinder, and a braze preform before assembly.
Figure 4B:
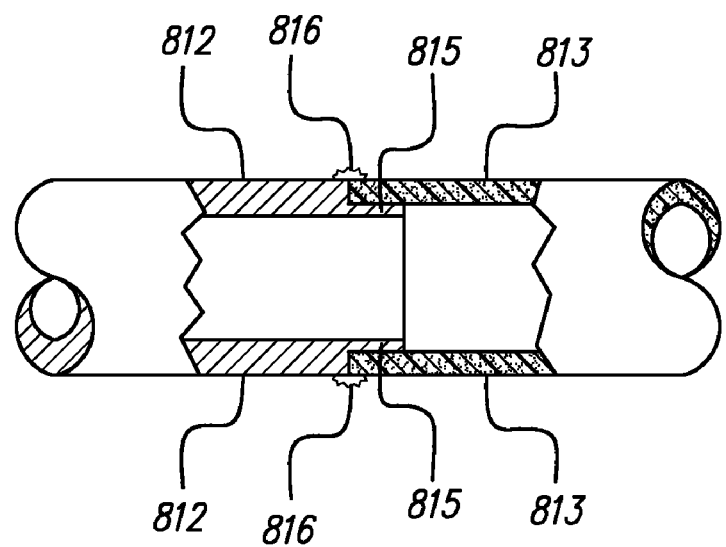
FIG. 4B is a cross-sectional view of the metal or metal alloy cylinder and the ceramic cylinder of FIG. 4A forming a self-jigging internal step joint after assembly.

FIG. 4A is a cross-sectional view of an assembly similar to that disclosed by the prior art of a metal or metal alloy cylinder 812, a ceramic cylinder 813, and a braze preform 814 before assembly. FIG. 4B is a cross-sectional view of the metal or metal alloy cylinder 812 and the ceramic cylinder 813 of FIG. 4A forming a self-jigging internal step joint after assembly. The self-jigging internal step joint is formed using the metal or metal alloy cylinder 812 which has a step with an internal flange 815. The internal flange 815 adjoins the interior surface of the ceramic cylinder 813.

The internal step joint of FIGS. 4A and 4B provides more lateral support and more surface area than the bevel and butt joints of FIGS. 2A to 3B. However, because the metal or metal alloy cylinder 812 and the ceramic cylinder 813 form an internal step joint with no external flange, the braze preform 814 melts during assembly and often exudes from the joint and cools after assembly to form a sharp ridge 816 of braze material along the exterior surface of the joint. The sharp ridge 816 should not be allowed to remain on the exterior surface of any consumer product, especially an implantable medical device. Permitting the sharp ridge 816 of metallic material to remain on the outer case of an implantable medical device would expose a patient to unnecessary danger. Therefore, it is important to remove the sharp ridge 816. Unfortunately, removing the sharp ridge 816 by machining or other process is certain to add time and expense to the assembly procedure and is very likely to weaken the braze joint as a result. An improvement upon the internal step joint of FIGS. 4A and 4B would prevent the sharp ridge 816 from ever forming during the braze assembly process. Such an improvement is provided by the present invention.

Figure 5A:
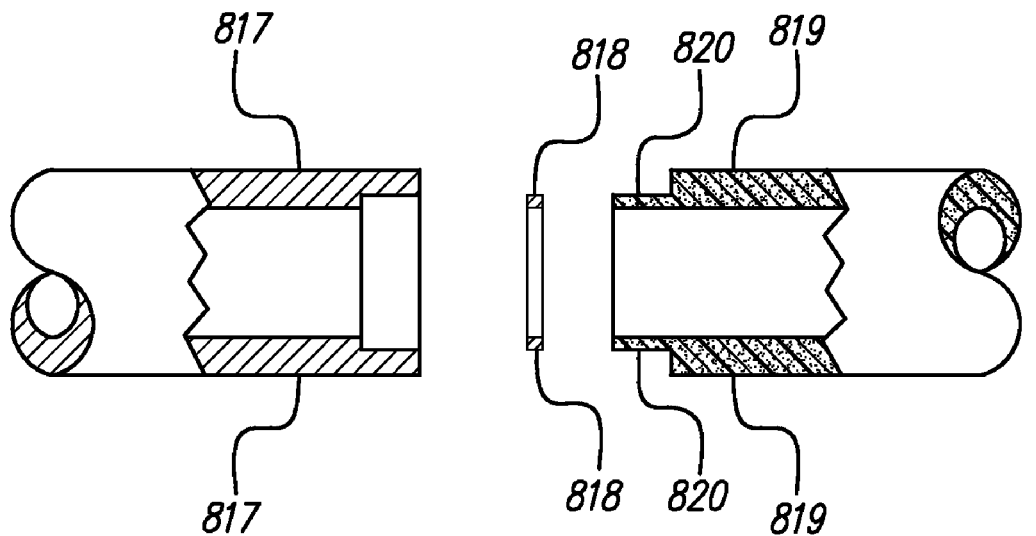
FIG. 5A is a cross-sectional view of an assembly similar to that disclosed by the prior art of a metal band, a metal braze material, and a ceramic sleeve with a machined flange before assembly.
Figure 5B:
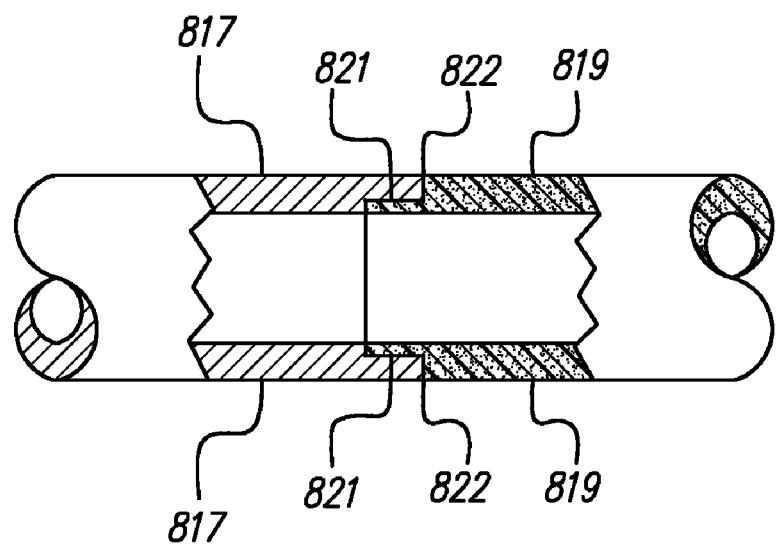
FIG. 5B is a cross-sectional view of the metal band and the ceramic sleeve with a machined flange of FIG. 5A after assembly.

FIG. 5A is a cross-sectional view of an assembly similar to that disclosed by the prior art of a metal band 817, a metal braze material 818, and a ceramic sleeve 819 with a machined flange 820 before assembly. FIG. 5B is a cross-sectional view of the metal band 817 and the ceramic sleeve 819 with a machined flange 820 of FIG. 5A forming a double step joint after assembly. The joint of FIGS. 5A and 5B provides increased surface area 821 for braze material, which may permit a braze joint to form without braze material exuding to the exterior 822 of the joint.

Although FIGS. 5A and 5B provide a joint with both increased surface area and the lateral support of a step-type joint, the joint unfortunately includes a machined ceramic member that is likely to result in a weak joint, especially where the ceramic member is thin. The machined flange of 820 is formed by machining the end of the ceramic sleeve 819. Machining a ceramic case often leaves residual cracks and weakens the case, especially where the wall of the ceramic case is thin, e.g., less than a few millimeters in thickness. A joint created using a ceramic case with a machined flange that is likely to crack or weaken is unacceptable for use with implantable medical devices or other devices in which a user places her trust. An improvement upon the double step joint of FIGS. 5A and 5B would avoid using a ceramic member with a machined flange to form the joint. Such an improvement is provided by the present invention.

Figure 6A:
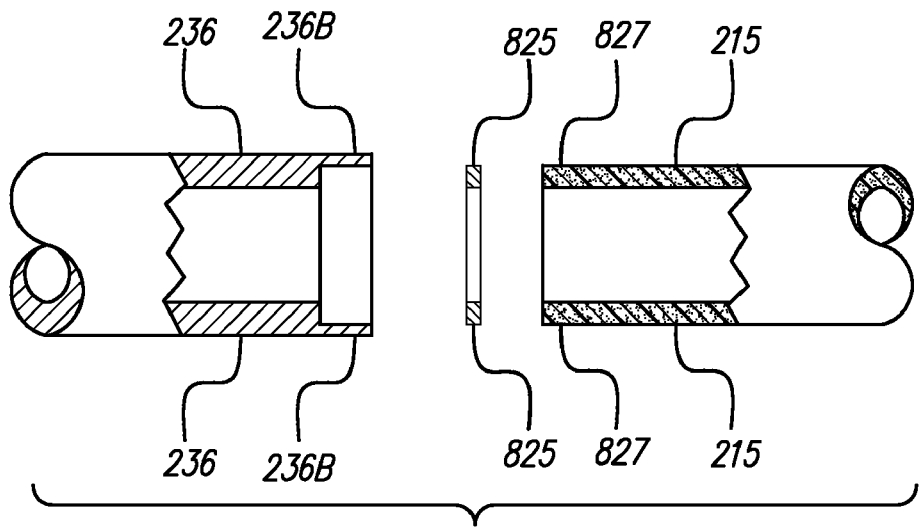
FIG. 6A is a cross-sectional view of the present invention of a metal ring with an external flange, a braze material, and a ceramic can before assembly.

FIGS. 6A to 7B represent embodiments of the present invention, the novel structures of which successfully overcome many of the difficulties encountered by the prior art by providing adequate surface area and lateral support in a braze joint with a ceramic member that need not be machined. FIG. 6A is a cross-sectional view of the present invention of a connector or metal ring 236 with an external flange 236B, a nickel-titanium braze material 825, and a ceramic can 215 with a formed end 827 before assembly. The formed end 827 need not be machined as shown in the prior art. In other words, after the can 215 is initially formed, the formed end 827 need not be cut or otherwise modified in a manner that increases the likelihood of residual cracks forming in the can 215. The formed end 827 may be any shape that forms a successful braze joint of the present invention. The braze material 825 can be any type of braze material suitable for brazing metal to ceramic material. In one embodiment, nickel and titanium sheets are placed on top of each other and rolled together during manufacturing. Later, the washer-shaped rings may be cut out to form the braze material 825.

Figure 6B:
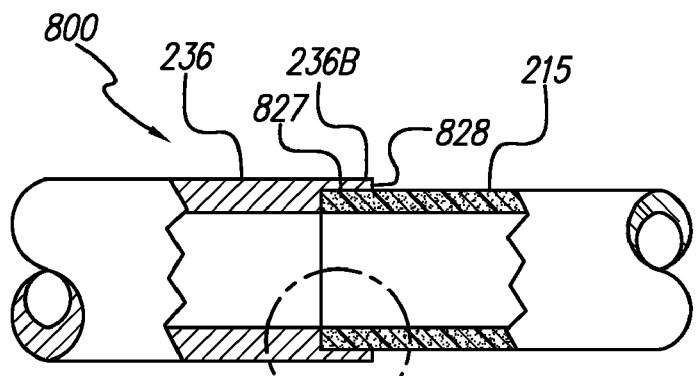
FIG. 6B is a cross-sectional view of the metal ring and the ceramic can of FIG. 6A forming a self-jigging external step joint after assembly.

FIG. 6B is a cross-sectional view of the metal ring 236 and the ceramic can 215 of FIG. 6A forming a self-jigging external step joint after assembly. External flange 236B, fitting snugly around the exterior circumferential surface of the formed end 827 of ceramic can 215, successfully serves to self-center the metal ring 236, the braze material 825, and the ceramic can 215 during assembly. External flange 236B further acts as a dam to prevent the braze material 825 from exuding to the exterior surface 828 of the joint.

Further, the surface area of the external step joint formed between the metal ring 236 and the ceramic can 215 provides adequate surface area for a sufficient amount of the braze material 825 to form a strong braze bond without exuding from the joint. The surface tension of the nickel titanium braze material 825 and the design of the joint serve to wick the braze material away from the inner diameter of the shell 800 toward the outer surface of the shell 800. However, because the present invention provides an increase surface area along which the braze material 825 may bond, an adequate amount of the braze material 825 is not wicked so far as to exude to the outer or inner surface of the shell 800. Even further, the step joint formed using the external flange 236B of the metal ring 236 provides adequate lateral support for the joint components to be assembled without the need for auxiliary components that provide additional lateral support. By eliminating the need for auxiliary components, the present invention reduces the amount of time, materials, and complexity of the braze joint assembly process.

Figure 6C:
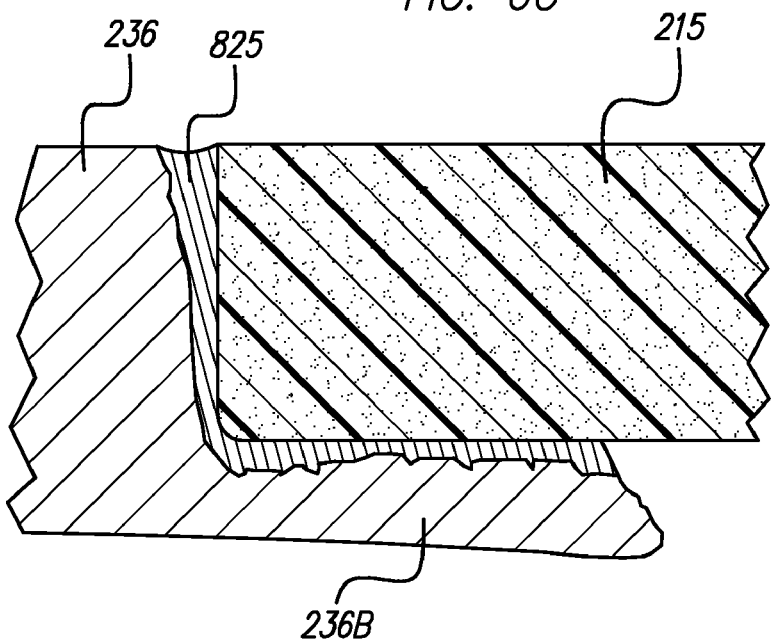
FIG. 6C represents an actual 200:1 enlarged view of a cross-section of the external step joint after assembly.

FIG. 6C represents an actual 200:1 enlarged view of a cross-section of the braze joint after assembly. The approach of FIGS. 6A and 6B has been tested and the actual results are portrayed in FIG. 6C. FIG. 6C shows the metal ring 236 with the external flange 236B successfully brazed to the ceramic can 215 using the braze material 825. The braze material 825, after melting and cooling during the braze process, is spread relatively evenly along the entire surface area between the metal ring 236 and ceramic can 215, forming a strong braze bond. The braze material 825 has not exuded beyond the end of the external flange 236B. By overcoming many of the challenges experienced in various teachings of the prior art in a single design, the present invention is a "small step" joint that represents a "giant leap" over the prior art.

Figure 7A:
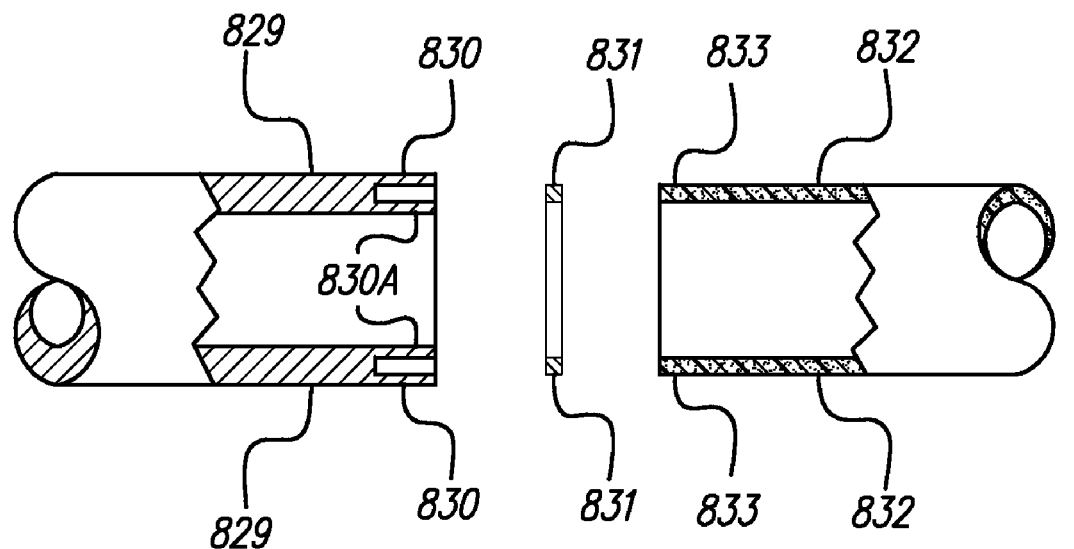
FIG. 7A is a cross-sectional view of the present invention of a metal ring with internal and external flanges, a braze material, and a ceramic can before assembly.
Figure 7B:
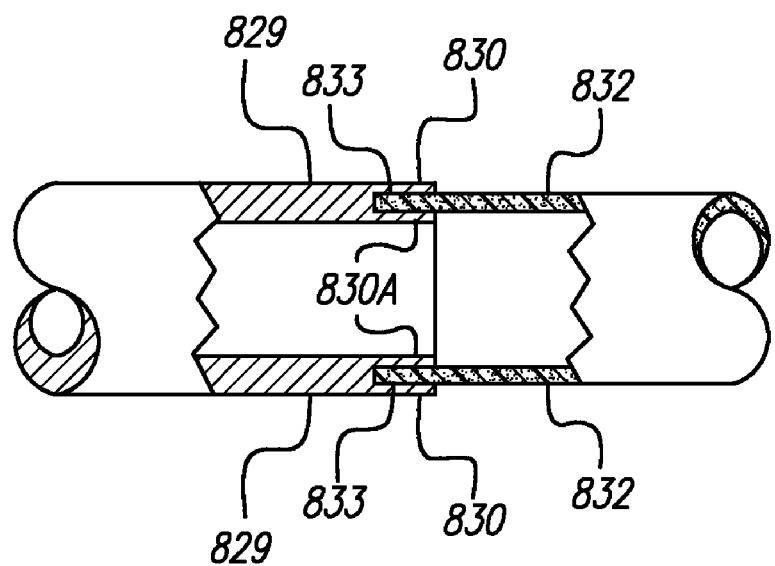
FIG. 7B is a cross-sectional view of the metal ring and the ceramic can of FIG. 7A forming a u-joint after assembly.

FIG. 7A is a cross-sectional view of another embodiment of the present invention of a metal ring 829 with internal and external flanges 830, a braze material 831, and a ceramic can 832 with a formed end 833 before assembly. FIG. 7B is a cross-sectional view of the metal ring 829 and the ceramic can 832 of FIG. 7A forming a u-joint after assembly. The embodiment of FIGS. 7A and 7B enjoys benefits of the structure of the embodiment shown in FIGS. 6A to 6C, namely: a metal ring 829 having a stepped end with an external flange 830 and a ceramic can 832 with a formed end 833. The embodiment of FIGS. 7A and 7B adds an internal flange 830A to the end of the metal ring 829 to present a potential improvement to the embodiment of FIGS. 6A to 6C and to illustrate that numerous other embodiments of the present invention are possible without exceeding the scope of the present invention as defined in the claims. The embodiments could include step joints, step-bevel joints, step-curve joints, and other variously configured joints with at least one external flange on the end of the metallic member and a formed end on the ceramic member.

Figure 8A:
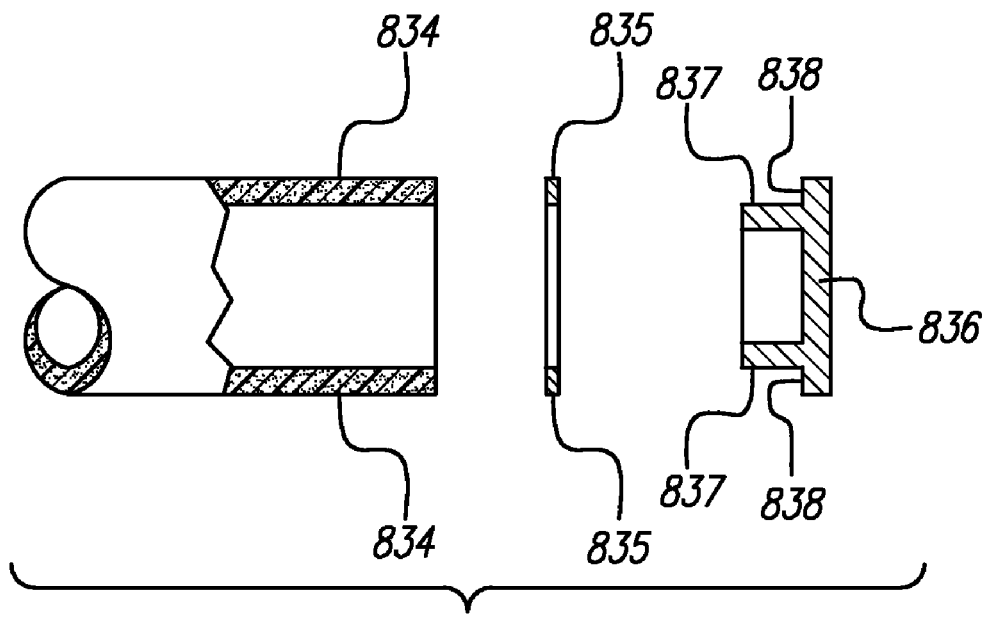
FIG. 8A is a cross-sectional view of an assembly similar to that disclosed by the prior art of an open-ended ceramic cylinder, a high temperature braze preform, and a metal end cap before assembly.
Figure 8B:
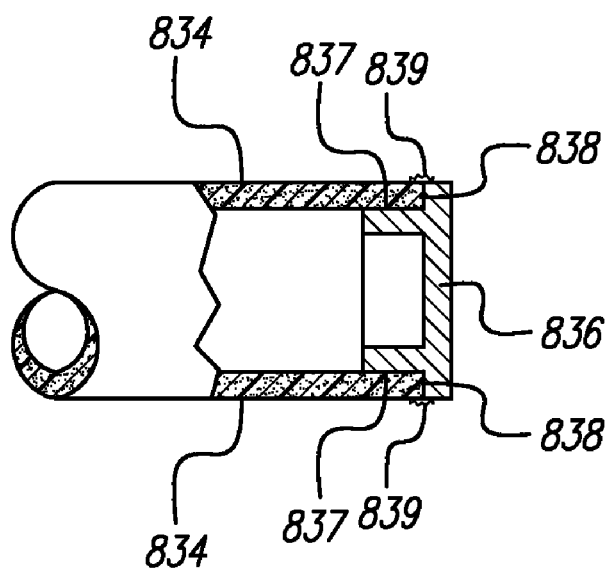
FIG. 8B is a cross-sectional view of the open-ended ceramic cylinder and metal end cap of FIG. 8A after assembly.

FIGS. 8A and 8B portray a braze joint, before and after assembly, that is similar to a braze joint disclosed by the prior art. FIG. 8A is a cross-sectional view of an assembly similar to that disclosed by the prior art of an open-ended ceramic cylinder 834, a high temperature braze preform 835, and a metal end cap 836 before assembly. The metal end cap 836 has a pin with a broad diameter 837 that results in a relatively narrow braze joint surface area 838.

FIG. 8B is a cross-sectional view of the open-ended ceramic cylinder 834 and metal end cap 836 of FIG. 8A after assembly. As a result of the pin with a broad diameter 837 and the narrow braze joint surface area 838 of the end cap 836, the braze preform 835 often melts during braze assembly and exudes out of the braze joint to form a sharp metal ridge 839 along the exterior surface of the braze joint. As mentioned earlier, the sharp metal ridge 839 is dangerous and should be removed. However, machining the sharp metal ridge 839 is often difficult and expensive, and is likely to weaken the braze joint. An improvement upon the braze joint of FIGS. 8A and 8B would prevent the sharp metal ridge 839 from forming during the assembly process. Such an improvement is provided by the present invention.

Figure 9A:
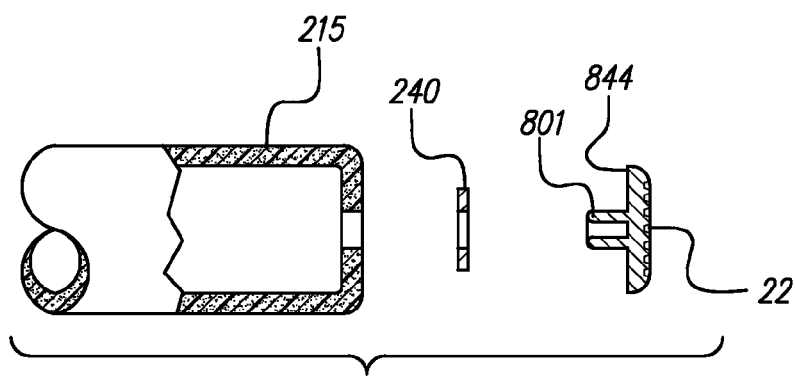
FIG. 9A is a cross-sectional view of the present invention of a close-ended ceramic can, a braze material, and an electrode before assembly.
Figure 9B:
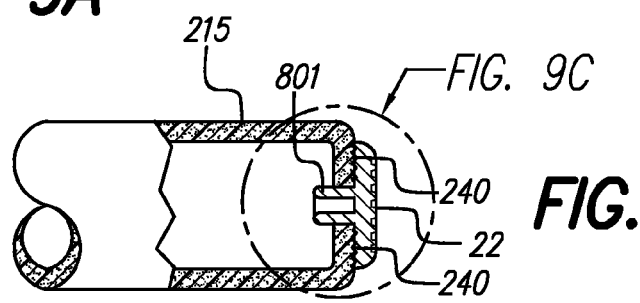
FIG. 9B is a cross-sectional view of the close-ended ceramic can, the braze material, and the electrode of FIG. 9A after assembly.
Figure 9C:
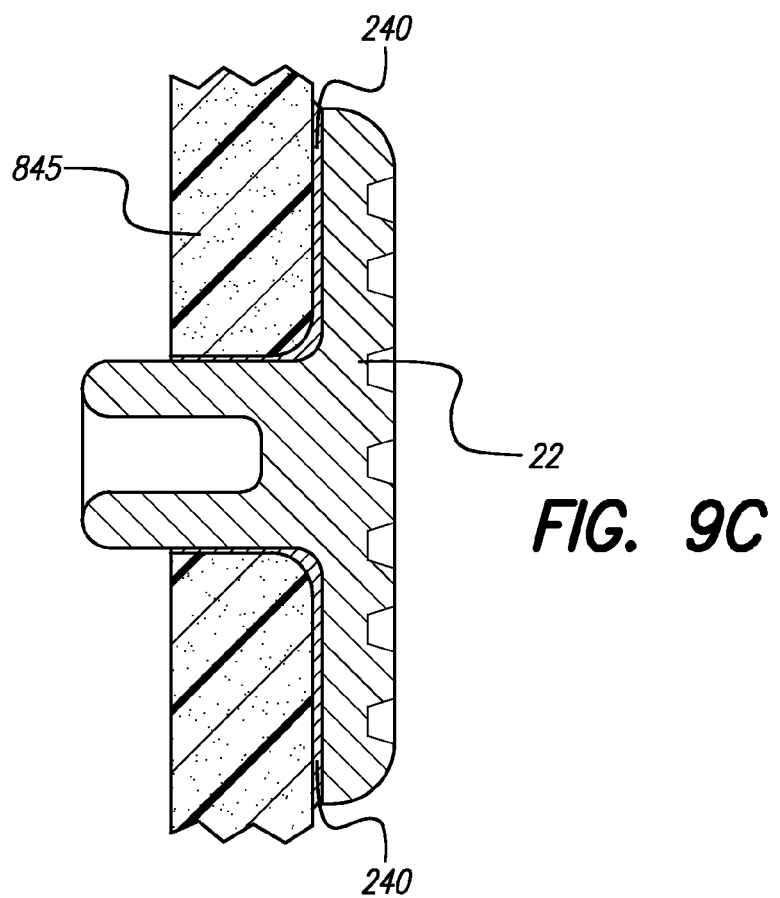
FIG. 9C represents an actual 50:1 enlarged view of a cross-section of the braze joint assembly after assembly.

FIGS. 9A to 9C represent embodiments of the present invention, the novel structures of which successfully overcome many of the difficulties encountered by the prior art, as exemplified in FIGS. 8A and 8B, by providing surface area adequate to create a strong braze joint while preventing braze material from exuding from the joint.

FIG. 9A is a cross-sectional view of the present invention of a ceramic can 215 with a closed end 845, a braze material 240, and an electrode 22 before assembly. The electrode 22 has a hollow pin with a narrow diameter 801 that results in a relatively broad braze joint surface area 844.

FIG. 9B is a cross-sectional view of the ceramic can 215 with the closed end 845, the braze material 240, and the electrode 22 of FIG. 9A after assembly. The pin 801 fits snugly into a hole in the end of the ceramic can 215. The closed end 845 adjoins the joint surface area 844 to provide a relatively broad surface area along which the braze material 240 forms a strong bond without exuding from the joint. The closed end 845 also provides greater support (than would an open end) against pressure along the axis of the braze joint assembly when the ceramic can 215 and the electrode 22 are compressed.

FIG. 9C represents an actual 50:1 enlarged view of a cross-section of the braze joint after assembly. The approach of FIGS. 9A and 9B has been tested and the actual results are portrayed in FIG. 9C. FIG. 9C shows the closed end 845 of the ceramic can 215 successfully brazed to the electrode 22 using the braze material 240. The braze material 240, after melting and cooling during the braze process, is spread relatively evenly along the entire surface area between the ceramic can 215 and the electrode 22, forming a strong braze bond. The braze material 240 has not exuded substantially beyond the end of the electrode 22. Less braze material 240 and/or less compression force between electrode 22 and ceramic can 215 may be applied in order to limited the distance that the braze material 240 is able to travel towards the exterior edge of the braze joint while creating an adequately strong braze bond.

Figure 10:
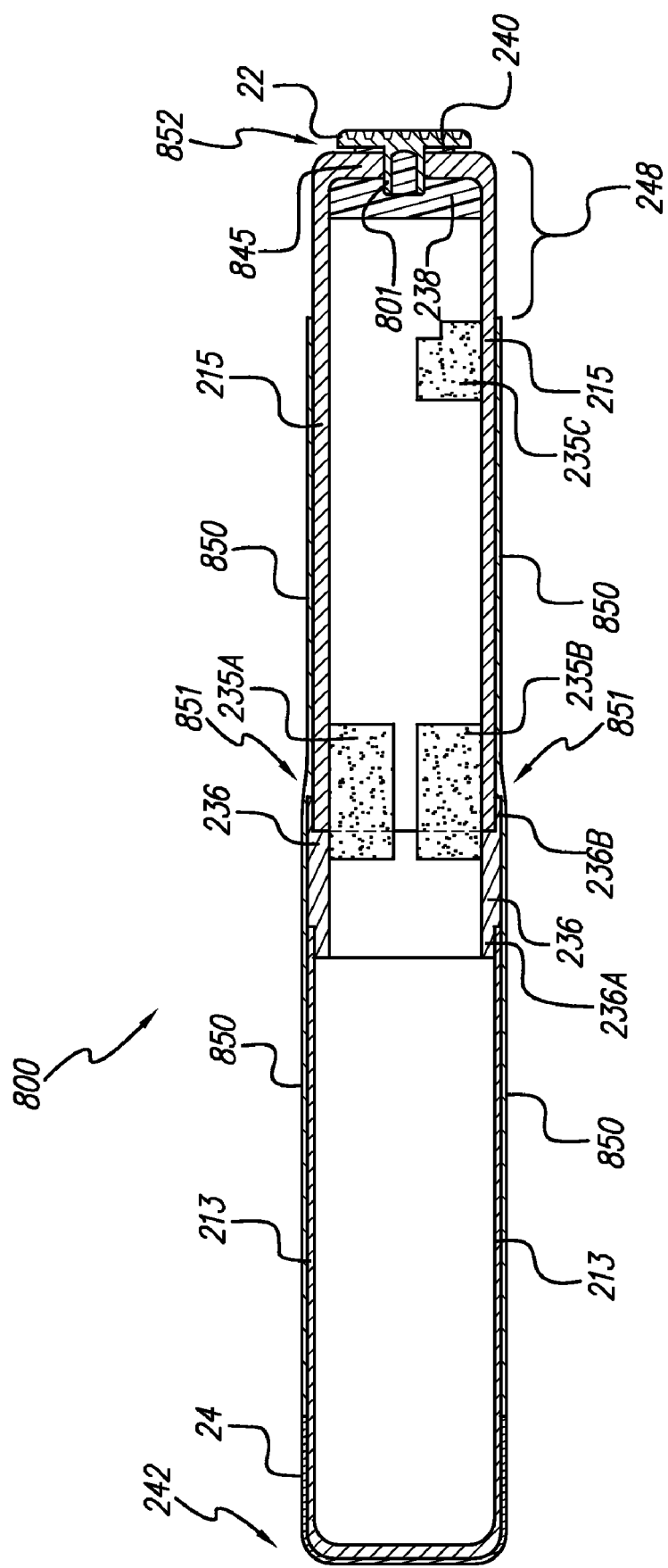
FIG. 10 is a cross-sectional view of the present invention of a Bion® case with a parylene coating.

FIG. 10 is a cross-sectional view of the Bion® microstimulator shell 800 of the present invention as shown in FIG. 1A with a parylene coating 850. A type C parylene or other suitable insulation coating 850 is applied to the exterior surface of shell 800 by standard masking and vapor deposition processes. The zirconia ceramic case is left exposed in area 248 and an iridium electrode 24 is shown on an end 242 of the case 213. FIG. 10 also shows two exemplary braze assemblies of the present invention as previously described. The braze assembly of FIGS. 6A to 6C is shown at braze assembly 851. The braze assembly of FIGS. 9A to 9C is shown at braze assembly 852.

Figure 11:
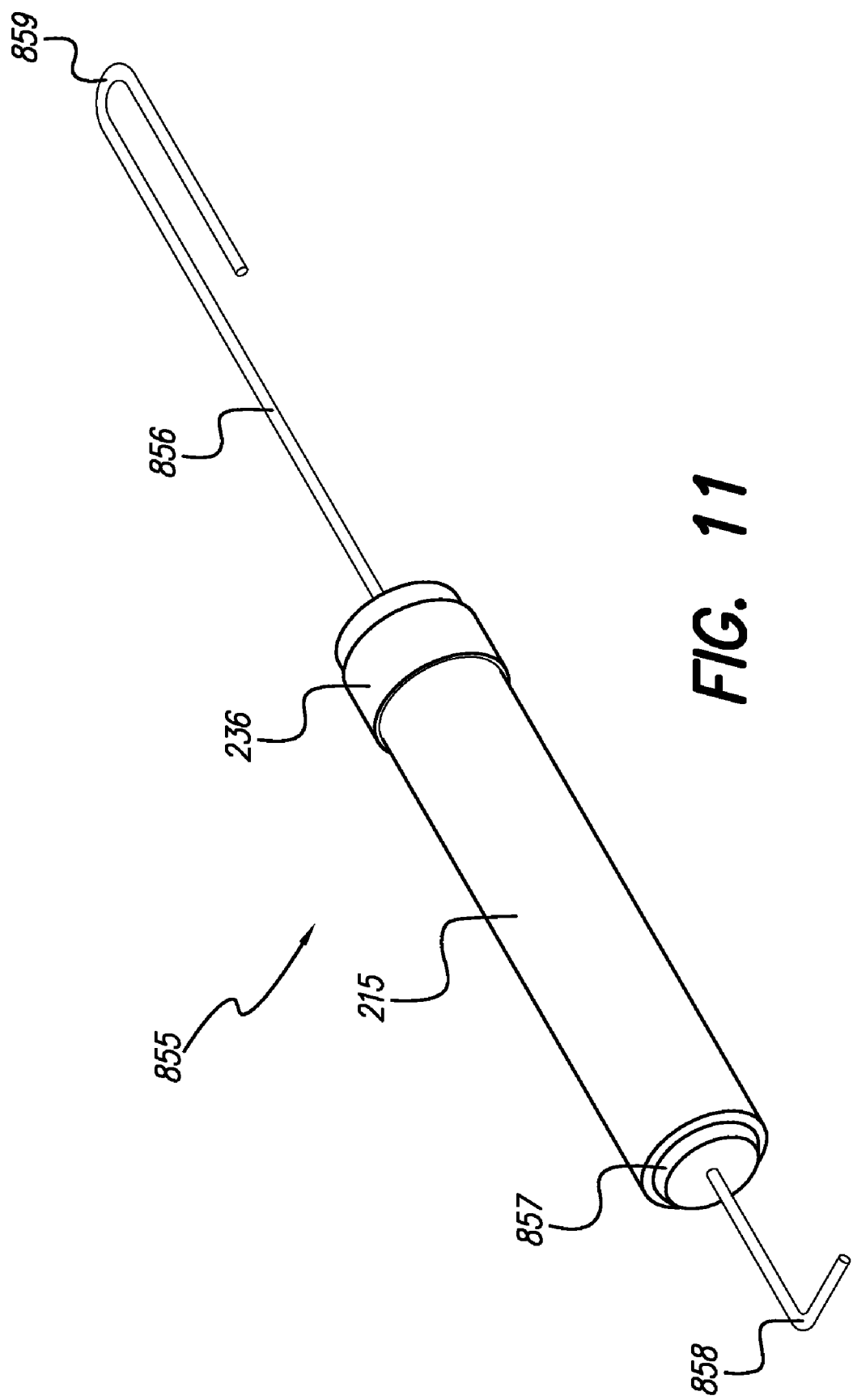
FIG. 11 is a perspective view of a completed braze assembly and a titanium wire.

FIG. 11 is a perspective view of a completed braze assembly 855 and a titanium wire 856. The completed braze assembly 855 includes the metal ring 236 brazed to the ceramic can 215, which in turn is brazed to an electrode 857 with a feed-through hole that has been drilled or otherwise formed or created through the center of the electrode 857. The electrode 857 is made of machined titanium or other conductive material. The center core of the electrode 857 through which the feed-through hole is drilled is preferably thin enough to allow a small diameter drill bit to drill a small diameter hole through the entire core without breaking or overheating the drill bit.

Before the titanium wire 856 is threaded through the braze assembly 855, and end of the titanium wire 856 is bent (or otherwise prepared, e.g., with a clip, ball, or other structure or bend capable of the same function) to form an elbow 858, so as to prevent the wire from sliding completely through the braze assembly 855 during threading. After the braze assembly 855 is completely assembled with the electrode 857, the end of the titanium wire 856 opposite the elbow 858 end is threaded through the core of the braze assembly 855. The wire 856 may be threaded from either end of assembly 855, but is preferably threaded beginning at the electrode 857 end. After the titanium wire 856 is threaded through the braze assembly 855, the end of the wire 856 that is opposite the elbow 858 end is bent to form a u-loop 859 or other substantially similar shape.

Figure 12:
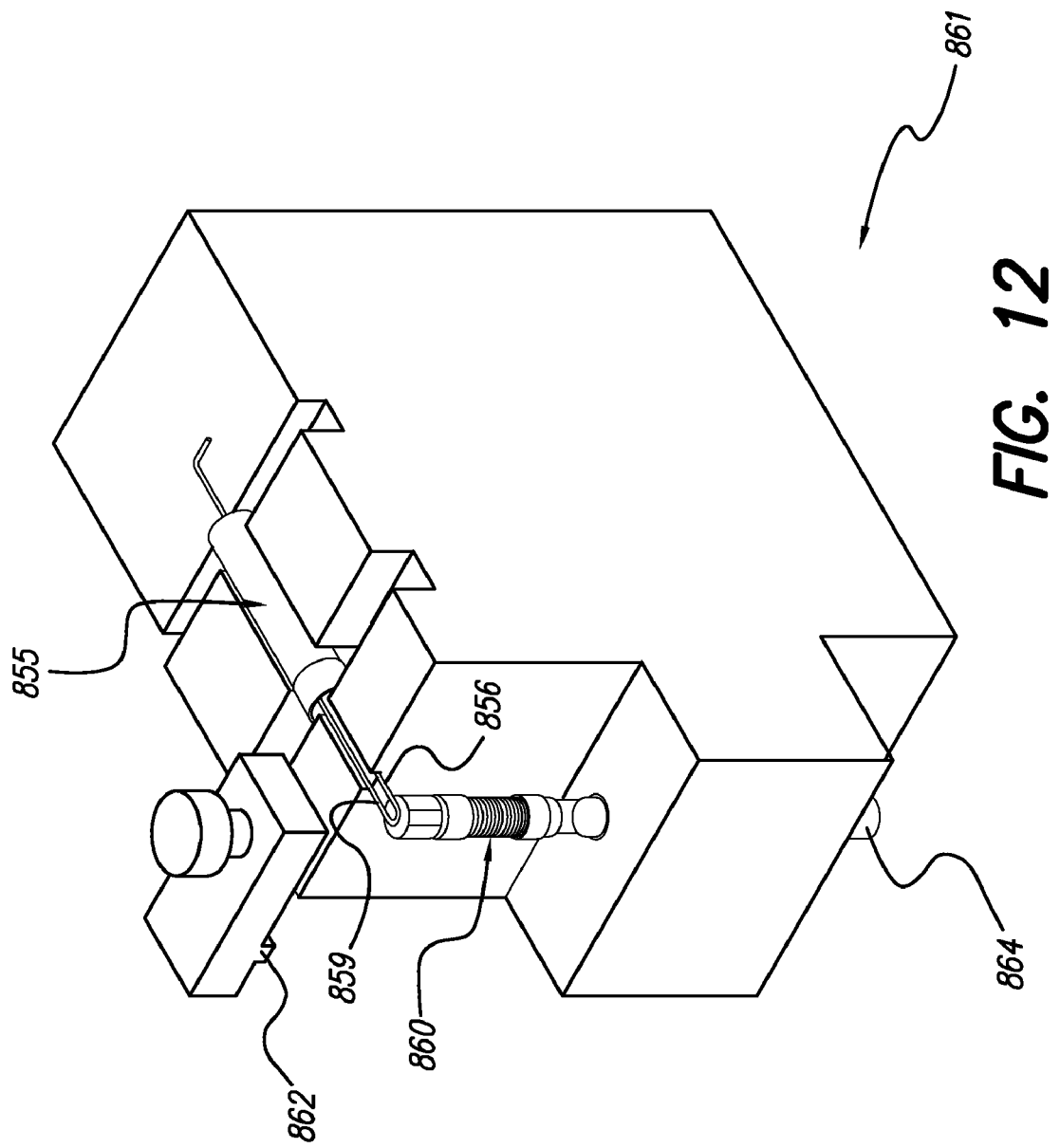
FIG. 12 is a perspective view of a completed braze assembly and the inner components of a microstimulator housed in a carrier.

FIG. 12 is a perspective view of a completed braze assembly 855 after threading, and other inner components 860 of a microstimulator housed and stabilized in an assembly carrier 861. The u-loop 859 protrudes from a groove 863 of the carrier 861. The u-loop 859 may be secured by a wedge 862 that pivots and is placed upon the u-loop 859. An elevator screw 864 is tightened in order to raise the inner components 860 until the top surface of a capacitor 865 of the inner components 860 touches the bottom surface of the u-loop 859. The u-loop 859 may be another shape that permits the u-loop 859 to come into maximum contact with the capacitor 865. Likewise, the components and the carrier 861 of FIG. 12 may be arranged in a variety of different manners so as to permit the u-loop 859 to come into maximum contact with the capacitor. Conductive epoxy, solder, or other similar material or method is used to create a permanent electrical connection between the u-loop 859 and the capacitor 865. The excess end of the wire 856 of u-loop 859 is removed.

Figure 13:
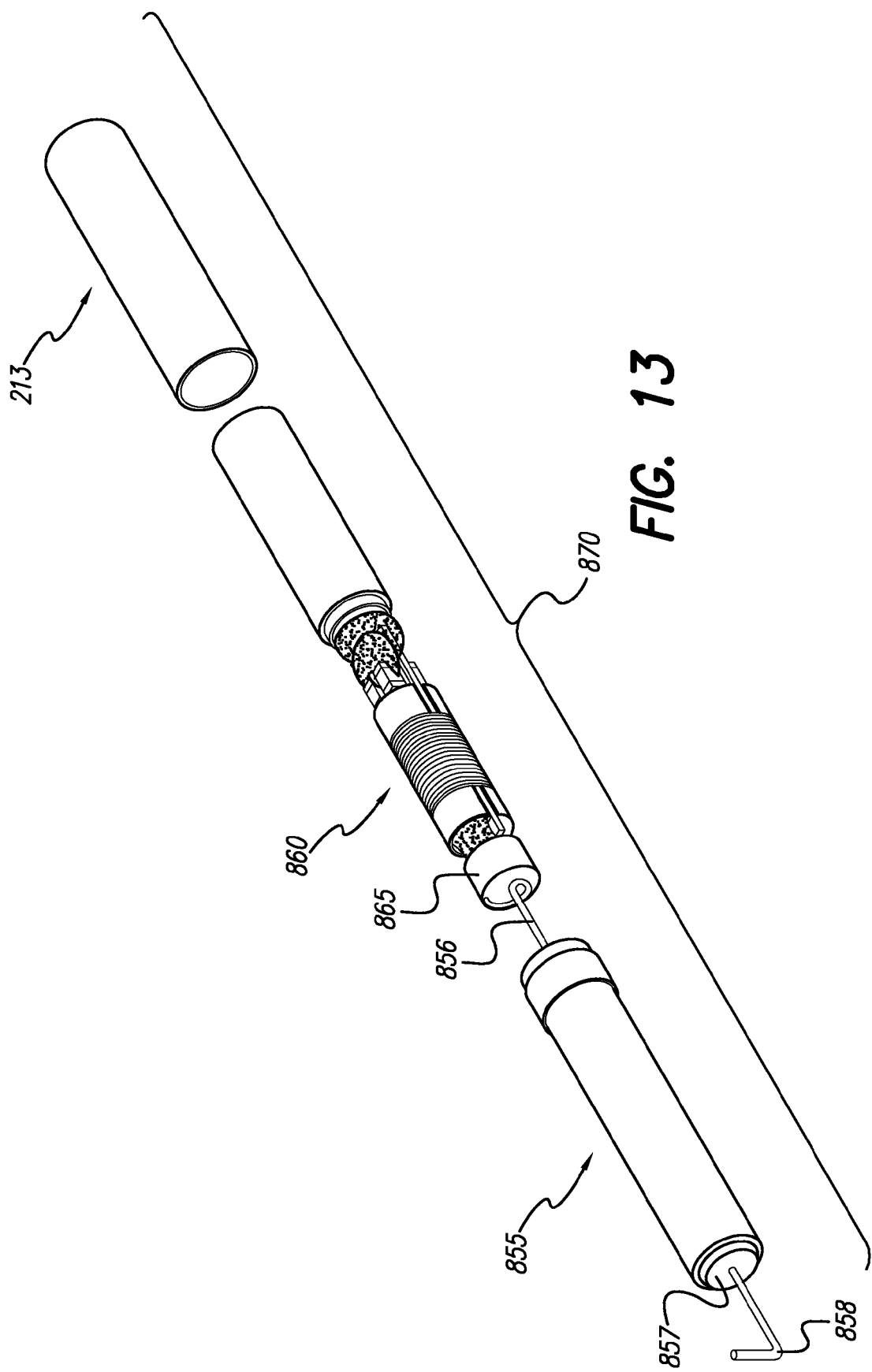
FIG. 13 is a perspective view of a microstimulator before final assembly.

FIG. 13 is a perspective view of a microstimulator 870 before final assembly. The wire 856 and the capacitor 865 are electrically attached to each other. The case 213 and the braze assembly 855 can now be slid over the body of the inner components 860. After the braze assembly 855 is slid over the inner components 860, the elbow 858 end of the wire 856 remains, exiting from the electrode 857.

FIG. 14 is a perspective view of a pre-assembled microstimulator 870 horizontally housed and secured in an assembly carrier 871. A spring-loaded base 872 compresses the microstimulator against the wall 873 of the carrier 871 so that the case 213 and the braze assembly 855 are firmly held together. The case 213 is then laser spot welded, or otherwise attached, to the braze assembly 855 at union 874. The microstimulator 870 is then rotated in the carrier 871 and the union 874 is spot welded, or otherwise attached, at other points along the circumference of the union 874. The microstimulator 870 is then removed from a horizontal position in the carrier 871 and placed into vertical position within a hole 875 in the carrier 871 and oriented with the electrode 857 and wire 856 exiting the hole 875, as shown in FIG. 15.

FIG. 15 is a perspective view of the microstimulator 870 vertically housed in the carrier 871. The wire 856 is laser spot welded, or otherwise electrically attached, to the electrode 857, resulting in an electrical connection between the electrode 857 and the capacitor 865 (FIG. 13). During the laser weld process, the excess wire 856 is cut and removed from the microstimulator 870. If the wire 856 is otherwise electrically attached to the electrode 857, the excess wire 856 is cut or otherwise removed in a manner consistent with the respective approach. Before the wire 856 is attached and removed, a preferred and appropriate amount of slack may be provided to the wire 856 in order to avoid wire disconnection during any thermal expansion of the microstimulator 870.

Figure 16:
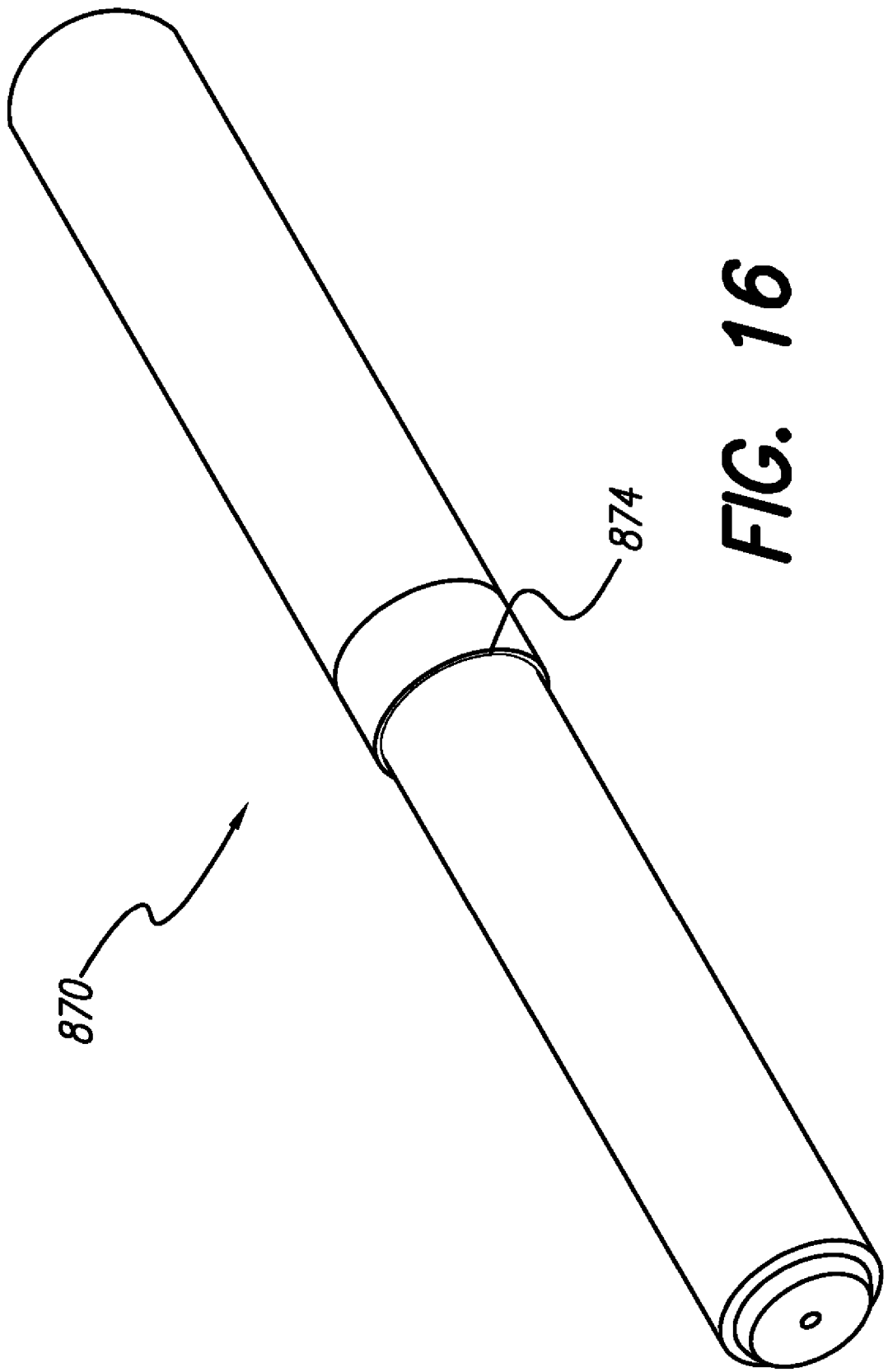
FIG. 16 is a perspective view of a microstimulator after final assembly.

FIG. 16 is a perspective view of a microstimulator 870 after final assembly. The microstimulator 870 has been laser welded, or otherwise permanently attached, along the entire circumference of union 874. The microstimulator 870 shown in FIG. 16 has been brazed, welded, and coated according to the teachings of the present invention.

The feed-through hole design and method of FIGS. 11 to 16 is an improvement upon other structures and methods used to electrically attach an electrode to the inner components of a hermetically-sealed microstimulator. The feed-through hole design and method of the present invention is a positive, mechanical connection that is completed after a case of a microstimulator is completely assembled, rather than before. By welding a wire to the electrode of the microstimulator after the case of the microstimulator is completely assembled, the electrical connection formed using the wire does not risk disconnection during a welding or brazing process. A welding or brazing process is likely to create thermal expansion, contraction, and mismatch of the different materials of the case, because the different materials have different thermal coefficients. Further, by welding a wire to the electrode of the microstimulator after the case of the microstimulator is completely assembled, a preferred and appropriate amount of slack may be provided to the wire in order to avoid wire disconnection during any future thermal expansion of the materials of the microstimulator.

While the invention herein disclosed has been described by means of specific embodiments and applications thereof, numerous modifications and variations could be made thereto by those skilled in the art without departing from the scope of the invention set forth in the claims.

What is claimed is:

1. A method of brazing an assembly, comprising:
    providing a ceramic member with an end, which end is formed without machining and which ceramic member includes zirconia, wherein an external diameter of the ceramic member is constant along a length of the ceramic member;
    providing a metal member including titanium and an exterior flange, the exterior flange having a uniform thickness along its length and configured to at least partially encompass the end of the ceramic member, wherein an internal diameter of the exterior flange is constant along a length of the exterior flange and wherein the internal diameter of the external flange is greater than the external diameter of the ceramic member and the thickness of the exterior flange is less than a thickness of an adjacent portion of the metal member;
    placing braze material between the metal member and the ceramic member, the braze material including titanium and nickel;
    compressing the metal member and the end of the ceramic member formed without machining together with the exterior flange at least partially encompassing the end of the ceramic member;
    heating the braze material, the metal member, and the ceramic member in a vacuum until the braze material forms a liquidus; and
    cooling the braze material, the metal member, and the ceramic member in the vacuum until the braze material forms a solidus.

2. The method of claim 1 wherein the ceramic member includes a substantially closed end.

3. The method of claim 2, wherein the step of placing the braze material between the metal member and the ceramic member further comprises the step of aligning the metal member with the braze material and the substantially closed end of the ceramic member.

4. The method of claim 2 wherein the substantially closed end is an electrode.

5. The method of claim 4 wherein the electrode further comprises: a broad-diameter braze surface adjoining the substantially closed-end of the ceramic member.

6. The method of claim 5 wherein the electrode further comprises:
    a narrow-diameter pin; and
    a stimulating surface with grooves that increase the surface area of the stimulating surface.

7. The method of claim 1 further comprising the following step: receiving the ceramic member into the exterior flange of the metal member before the steps of compressing, heating, and cooling.

8. The method of claim 7 wherein the exterior flange provides lateral support to ceramic member during the steps of compressing, heating, and cooling.

9. The method of claim 1 wherein the step of placing further includes placing an amount of braze material between the metal member and the ceramic member, which amount of braze material is capable of forming a strong braze bond without exuding from between the metal member and the ceramic member.

10. A method of brazing an assembly, comprising:
providing a first metal member including an exterior flange of the first metal member, the exterior flange including an inner surface and a uniform thickness along its length, wherein an internal diameter of the exterior flange is constant along a length of the exterior flange;
providing a braze material including titanium and nickel;
providing a ceramic member including a formed end, wherein an external diameter of the ceramic member is constant along a length of the ceramic member and wherein the internal diameter of the exterior flange is greater than the external diameter of the ceramic member and the thickness of the exterior flange is less than a thickness of an adjacent portion of the metal member;
holding the formed end of the ceramic member adjacent the inner surface of the exterior flange of the first metal member so that the exterior flange at least partially encompasses the formed end of the ceramic member; and
brazing the first metal member to the ceramic member with the braze material where the formed end of the ceramic member and the inner surface of the exterior flange of the first metal member are held together.

11. The method of claim 10 wherein the ceramic member is a substantially close-ended ceramic can and includes a second metal member which forms an end cap to the ceramic member, which end cap completely closes the end of the ceramic can.

12. The method of claim 11 wherein the end cap is an electrode.

13. The method of claim 12 wherein the electrode further comprises: a broad-diameter braze surface adjoining the substantially closed-end of the ceramic member.

14. The method of claim 13 wherein the electrode further comprises:
a narrow-diameter pin; and
a stimulating surface with grooves that increase the surface area of the stimulating surface.

15. The method of claim 12 wherein the electrode further comprises:
a narrow-diameter pin; and
a stimulating surface with grooves that increase the surface area of the stimulating surface.

16. The method of claim 10 wherein the braze assembly is used to hermetically seal the shell of a microstimulator.

17. The method of claim 10 wherein the exterior flange forms a 90° angled step with an adjacent portion of the first metal member against which the formed end of the ceramic member may be received, and wherein the surface area between the first metal member and the ceramic member is capable of receiving an adequate amount of braze material to form a strong braze bond.

18. The method of claim 10 wherein the exterior flange provides lateral support to the braze assembly.

19. The method of claim 1, wherein the ceramic member is a cylinder, the metal member is a cylinder having a uniform outer diameter along a length of the metal member, and the outer diameter of the metal member and the inner diameter of the exterior flange are both greater than the outer diameter of the ceramic member.

20. The method of claim 10, wherein the ceramic member comprises an interior surface and the exterior flange comprises an inner surface, and wherein the interior surface of the portion of the ceramic member encompassed by the exterior flange is parallel to the inner surface of the exterior flange.

* * * * *